(12) United States Patent
Hsung et al.

(10) Patent No.: US 7,981,264 B2
(45) Date of Patent: Jul. 19, 2011

(54) DRIFT CALIBRATION METHOD AND DEVICE FOR THE POTENTIOMETRIC SENSOR

(75) Inventors: Shen-Kan Hsung, Jhongli (TW); Jung-Chuan Chou, Douliou (TW); Tai-Ping Sun, Jhongli (TW); Chung-We Pan, Pintung County (TW); Chu-Neng Tsai, Chia I County (TW)

(73) Assignee: Chung Yuan Christian University (TW)

( * ) Notice: Subject to any disclaimer, the term of this patent is extended or adjusted under 35 U.S.C. 154(b) by 1315 days.

(21) Appl. No.: 11/349,947

(22) Filed: Feb. 9, 2006

(65) Prior Publication Data
US 2007/0084721 A1    Apr. 19, 2007

(30) Foreign Application Priority Data
Oct. 18, 2005  (TW) .............................. 94136316 A

(51) Int. Cl.
*G01N 27/26*    (2006.01)

(52) U.S. Cl. ........................................ 204/406; 204/401
(58) Field of Classification Search .................. 204/401, 204/406, 435; 257/262; 438/199, 49, 48, 438/104, 197; 29/875; 205/777; 436/106, 436/96
See application file for complete search history.

(56) References Cited

U.S. PATENT DOCUMENTS

| | | | |
|---|---|---|---|
| 6,370,941 B2 * | 4/2002 | Nakamura et al. | 73/31.05 |
| 2003/0218194 A1 * | 11/2003 | Chou et al. | 257/288 |
| 2004/0185591 A1 * | 9/2004 | Hsiung et al. | 438/49 |
| 2005/0139490 A1 * | 6/2005 | Chou et al. | 205/777 |

* cited by examiner

*Primary Examiner* — Ula C Ruddock
*Assistant Examiner* — Gurpreet Kaur
(74) *Attorney, Agent, or Firm* — Bacon & Thomas, PLLC

(57) ABSTRACT

The present invention discloses a method and an apparatus of the drift calibration of sensors. The method includes shifting the sensing signal and differential technology to remove the drift signal by time during a long measuring. The apparatus includes two voltage sensors and readout circuits, a signal-shifting circuit and a differential circuit, and the apparatus is used for outputting the response signal without time drifting.

15 Claims, 5 Drawing Sheets

DRIFT CALIBRATION METHOD AND DEVICE FOR THE POTENTIOMETRIC SENSOR

BACKGROUND OF THE INVENTION

1. Field of the Invention

The present invention relates to a method of calibrating sensor, and more particularly to calibrate the drift signal that is outputted from the potentiometric sensors during a long-time measuring.

2. Description of the Prior Art

The direct measurement of the hydrogen ion activity (pH) of the aqueous solution, by means of the glass membrane electrode, has been a valuable technology in analytical chemistry and process monitoring for many years. Due to wet storage, fragility, big size and high cost, the solid-state electrodes have been developed to substitute for the glass electrode.

In 1970, the first ion-sensitive field-effect transistor (ISFET) was fabricated by Bergveld (please refer to reference [1]: P. Bergveld, entitled "Development of an ion-sensitive solid state device for neurophysiological measurements", IEEE Transactions on Bio-medical Engineering, vol. BME-17, pp. 70-71, 1970.). There are some advantages such as miniaturization, high input impedance and fast response of the ISFET. Furthermore, based on fast response, dry storage and low cost, the metal oxide electrode was investigated to substitute for the glass electrode by Fog and Buck (please refer to reference [2]: A. Fog, R. P. Buck, entitled "Electronic semiconducting oxides as pH sensors", Sensors and Actuators, vol. 5, pp. 137-146, 1984.)

In the progress of technology, requirements of environment monitoring, home care, and automation industry stimulate the development of sensors. Biosensors are especially employed on clinical diagnosis. The drift, which is the inherent drawback of the sensor, results in the shift of the output signal of the sensor with time under the solution of constant composition and temperature.

For long-term measurement, the drift causes unstable signal and handicaps the wide application of sensors especially in the environment, which needs high accuracy (the corresponding reference [3] is published by L. Bousse, D. Hafeman, N. Tran, entitled "Time-dependence of the chemical response of silicon nitride surfaces", Sensors and Actuators B, vol. 1, pp. 361-367, 1990., and further articles can be referred, for example, reference [4]: D. Yu, Y.-D. Wei, G.-H. Wang, "Time-dependent response characteristics of pH-sensitive ISFET", Sensors and Acruators B, vol. 3, pp. 279-285, 1991., reference [5]: A. Garde, J. Alderman, W. Lane, "Improving the drift and hysteresis of the Si3N4 pH response using RTP techniques", Sensors and Materials, vol. 9, pp. 15-23, 1997., reference [6]: P. Woias, L. Meixner, P. Frostl, "Slow pH response effects of silicon nitride ISFET sensors", Sensors and Actuators B, vol. 48, pp. 501-504, 1998., reference [7]: S. Jamasb, S. Collins, R. L. Smith, "A physical model for drift in pH ISFETs", Sensors and Actuators B, vol. 49, pp. 146-155, 1998., reference [8]: J. Hendrikse, W. Olthuis, P. Bergveld, "A method of reducing oxygen induced drift in iridium oxide pH sensors", Sensors and Actuators B, vol. 53, pp. 97-103, 1998., reference [9]: R. Kuhnhold, H. Ryssel, "Modeling the pH response of silicon nitride ISFET devices", Sensors and Actuators B, vol. 68, pp. 307-312, 2000., reference [10]: J.-C. Chou, C.-N. Hsiao, "Drift behavior of ISFETs with a-Si: H-SiO2 gate insulator", Materials Chemistry and Physics, vol. 63, pp. 270-273, 2000., reference [11]: S. Jamasb, entitled "An analytical technique for counteracting drift in ion-sensitive field effect transistors (ISFETs)", IEEE Sensors Journal, vol. 4, pp. 795-801, 2004.). The present invention provides a method of the drift calibration and the method is performed on the circuit to improve the long-term stability of potentiometric sensors.

Some prior arts disclosed these techniques, in United States patent, U.S. Pat. No. 4,701,253 to Hendrikus C. G. Ligtenberg, Jozef G. M. Leuveld, Date of patent: Oct. 20, 1987, entitled "ISFET-Based measuring device and method for correcting drift" provided an apparatus of the drift calibration for ISFETs. More particularly, the measuring device comprises an ISFET used as a chemically selective ion sensor, a reference electrode positioned adjacent the ISFET, an amplifier coupled to ISFET and control/correction circuitry coupled to ISFET, to the reference electrode and to the amplifier. The control/correction circuitry is operable to maintain the drain-source current IDS of the ISFET at a constant value and to correct drift effect of the ISFET on the basis of the logarithmic equation: $\Delta Vp = A \ln(t/t0+1)$, where: $\Delta VP$ is potential drift, A means scale factor for drift and amplitude, t0 is time constant defining the dependence on time, t indicates the time during which the sensor is operative in the event of continuous operation.

Another prior art disclosed by Hendrik H. v. d. Vlekkert, Nicolass F. de Rooy in the United States patent, U.S. Pat. No. 4,691,167, Date of patent: Sep. 1, 1987, entitled "Apparatus for determining the activity of an ion (pIon) in a liquid". The patent provided an apparatus for determining the activity of an ion. The device comprises a measuring circuit including an ISFET, a reference electrode adjacent the ISFET, a temperature sensor, and control, computing and memory circuits coupled to the amplifiers and operable to maintain two of the following three parameters, Vgs (gate-source potential), Vds (drain-source potential) and ID (drain-source current) at a constant value so that the third parameter can be used for determining the ion activity or pIon. The pIon sensitivity of the apparatus, as a function of temperature and/or the variation of the drain-source current, ID, as a function of the temperature are controlled by controlling the Vgs so that the pIon can be calculated from a formula stored in the memory.

Furthermore, Avron I. Bryan, Michael R. Cushman disclosed the relating technology in the United States patent, U.S. Pat. No. 5,046,028, Date of patent: Sep. 3, 1991, in titled of "System for calibrating, monitoring and reporting the status of a pH sensor". They provided a device for use in a system for providing on-line, real-time monitoring of the condition of a sensor immersed in a process solution. The sensor has a membrane and knows changes in characteristics of the process solution adjacent the membrane by periodically generating. The devices provide a fixed volume of the process solution adjacent the membrane and the fixed volume is independent of a flow rate of the process solution. The devices include a shield of non-conductive material, and have a retracted position permitting flow of the process solution past membrane to provide a fixed, stationary volume of process solution adjacent said membrane. The shield is selectively moved from its retraced position to its extended position during monitoring of the condition of the sensor.

Katsuhiko Tomita, Tsuyoshi Nakanishi, Syuji Takamatsu, Satoshi Nomura, Hiroki Tanabe, United States patent, U.S. Pat. No. 5,814,280, Date of patent: Sep. 29, 1998, in titled of "Semiconductor pH sensor and circuit and method of making same" provided a method to make pH sensor and circuit on the same substrate. A pH sensor having an ISFET is provided on a crystalline substrate of silicon with a thin film of aluminum oxide formed to have epitaxial growth with an overlaying thin film of silicon epitaxial grown on the aluminum oxide layer. A source element and a drain element are provided on the silicon film, and a pH responsive film layer is connected to the source and drain. The pH sensor can be accompanied with appropriate circuitry also integrally formed on the same epitaxial SOI substrate.

Please also refer to United States patent, U.S. Pat. No. 6,464,940, Date of patent: Oct. 15, 2002 to Koji Akioka, Akira Sanjoh, entitled "pH sensor and pH measurement method employing the same". The prior art provided a pH sensor, which is capable of readily determining the pH of a solution of a small amount. The pH sensor includes a semiconductor substrate, an oxide film provided on the semiconductor substrate, a solution storage part for holding a solution on the oxide film, and an electrode to be in contact with the solution in a vicinity of the oxide film. To determine the pH of a solution, a capacitance-voltage characteristic is initially monitored by the sensor between the electrode in contact with the solution and another electrode provided on the back surface of the semiconductor. Then the pH of the solution is derived from a flat band voltage, which is obtained based on the capacitance-voltage characteristic.

Torsten Poechstein, United States patent, U.S. Pat. No. 6,624,637' Date of patent: Sep. 23, 2003, in titled of "Device for measuring the concentrations in a measuring liquid" provided a device for measuring the concentration of hydrogen ions. The invention relates to a device for measuring the concentration of ions, notably of hydrogen ions, in a measuring liquid using at least one ion-sensitive field effect transistor which is integrated into an electric circuit within the device in such a way that said circuit emits an output signal which serves as measurement of the ion concentration in the measuring liquid. To provide a circuit which is as simple as possible, the invention provides for the at least one pH-ISFET to be bridge-connected with at least three resistors.

SUMMARY OF THE INVENTION

While the present invention will be described more fully hereinafter with some practice embodiments, it needs to pay more attention not only on these fully illustration but also this invention can be executed on a broad range embodiments. Furthermore, this invention is not limited by hereinbefore embodiments, it needs to depend on range of the patent claimed.

This invention discloses an auto-assembling system to assemble the frames and covers for the small shell devices.

Another purpose of this invention is to provide one auto-assembling system to combine the control circuit to control the transportation and assemble the frames and covers to assemble the small shell devices; it can also collect the frames and covers composition more efficient.

One more purpose of this invention is to provide an auto-assembling system, it is not only to increase the frames and covers assembly yield rate, also can reduce the equipment cost and improve the productivity and efficient.

This invention discloses an apparatus for sensor calibration, comprising: a first sensing element located in a monitoring solution for outputting a first sensing signal. A second sensing element located in a monitoring solution for outputting a second sensor signal. A first operation amplifier is utilized for outputting the first sensing signal, wherein a first input end of the first operation amplifier connects to the first sensing element and a second input end connects to ground. A second operation amplifier is employed for outputting the second sensing signal, wherein a third input end of the second operation amplifier connects to the second sensing element, and a fourth input end connects to ground. A voltage shifting circuit connects to the output end of the second operation amplifier for shifting the second operation sensing signal and outputting a third signal. The apparatus includes a third operation amplifier having a fifth input end that connects to the output end of the first sensing element, and a sixth input end that connects to the voltage shifting circuit for obtaining the potential difference between the first sensing signal and the third signal. A reference element is located in a monitoring solution, wherein one end of the reference element connects to ground for providing a constant voltage.

The first sensing element comprises potentiometric sensor including potentiometric $SnO_2$ pH sensor and potentiometric ammonium ISE sensor. The second sensing element comprises potentiometric sensor including potentiometric $SnO_2$ pH sensor and potentiometric ammonium ISE sensor. The first operation amplifier includes the instrumentation amplifier and the differential amplifier. The second operation amplifier includes the instrumentation amplifier and the differential amplifier. The voltage shifting circuit comprises a feedback circuit. The third operation amplifier includes the instrumentation amplifier and the differential amplifier. The reference element includes Ag/AgCl reference electrode. The first input end is positive input end. The second input end is negative input end. The third input end is positive input end. The fourth input end is negative input end. The fifth input end is positive input end. The sixth input end is negative input end.

This invention discloses a method for sensor calibration, comprising: obtaining a first signal and obtaining a second signal. Then, the method shifts the response voltage of the second signal to zero to obtain a third signal. The next step is to obtain a fourth signal from the first signal minus the third signal. Wherein said first signal is the potentiometric sensor signal. Wherein said second signal is the potentiometric sensor signal.

BRIEF DESCRIPTION OF THE DRAWINGS

Some of the purposes and advantages of the invention have been fully stated, others will be more fully understood by reference to the accompanying drawings, in which.

DESCRIPTION OF THE PREFERRED EMBODIMENT

Some sample embodiments of the invention will now be described in greater detail. Nevertheless, it should be recognized that the present invention can be practiced in a wide range of other embodiments besides those explicitly described, and the scope of the present invention is expressly not limited expect as specified in the accompanying claims. Then, the components of the different elements are not shown to scale. Some dimensions of the related components are exaggerated and meaningless portions are not drawn to provide clearer description and comprehension of the present invention.

Figure 1:
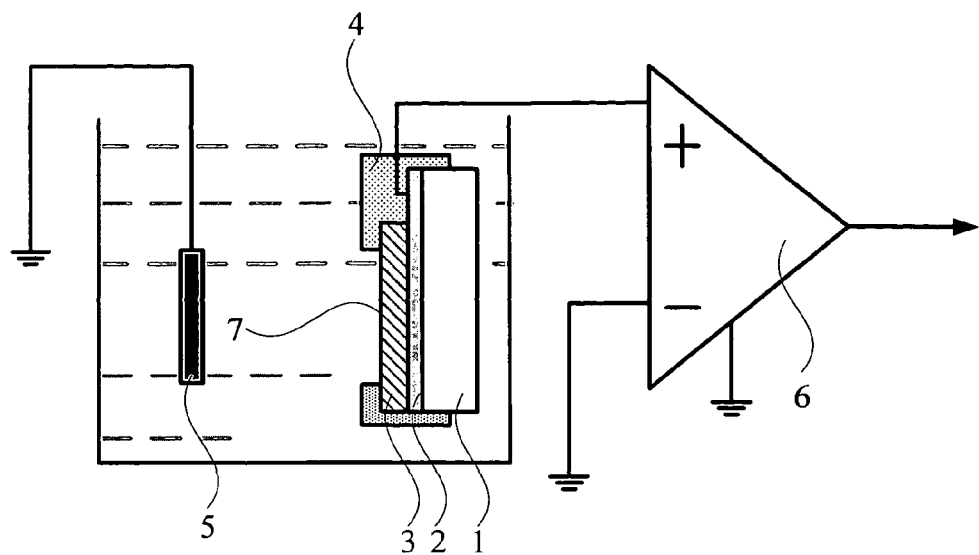
FIG. 1 is a readout circuit of the tin oxide pH sensor.

Referring to FIG. 1, showing a readout circuit of the potentiometric sensor, wherein the sensing element 30 connects to positive input end of an instrumentation amplifier 6, and the sensing element 30 is used to transform the pH value of a measuring solution 31 to a parameter such as voltage and transfer to positive input end of the instrumentation amplifier 6. A reference electrode 5 with one end connecting to ground is used to apply fixed reference voltage. The negative input end connects to ground, which is used to output the sensing signal related to pH value of the sensing solution 31.

The sensing element 31 includes a substrate 1, and the material of the substrate 1 can be glass or the like. The substrate 1 is covered by a conductive film 2, and the material of the conductive film 2 includes ITO (indium tin oxide) which can be obtained by well known technology. Besides, the glass substrate can be replaced by a ceramic substrate and a silicon substrate. A sensing film deposits onto the conductive film 2, which can be $SnO_2$ film formed by radio frequency sputtering method of semiconductor process technology. An insulating layer 4 covers over the peripheral of the ITO/$SnO_2$/glass structure for fixed, insulating and supporting, and the portion of sensor uncovered by the insulating layer 4 can measure and contact with the measuring solution. The material of the insulating layer 4 can be resin, compound, epoxy, silicone, silicone rubber, silicone resin, elastic PU, porous PU, acrylic rubber, blue tape, UV tape, plastic, epoxy resin, water-resist tape.

Figure 2:
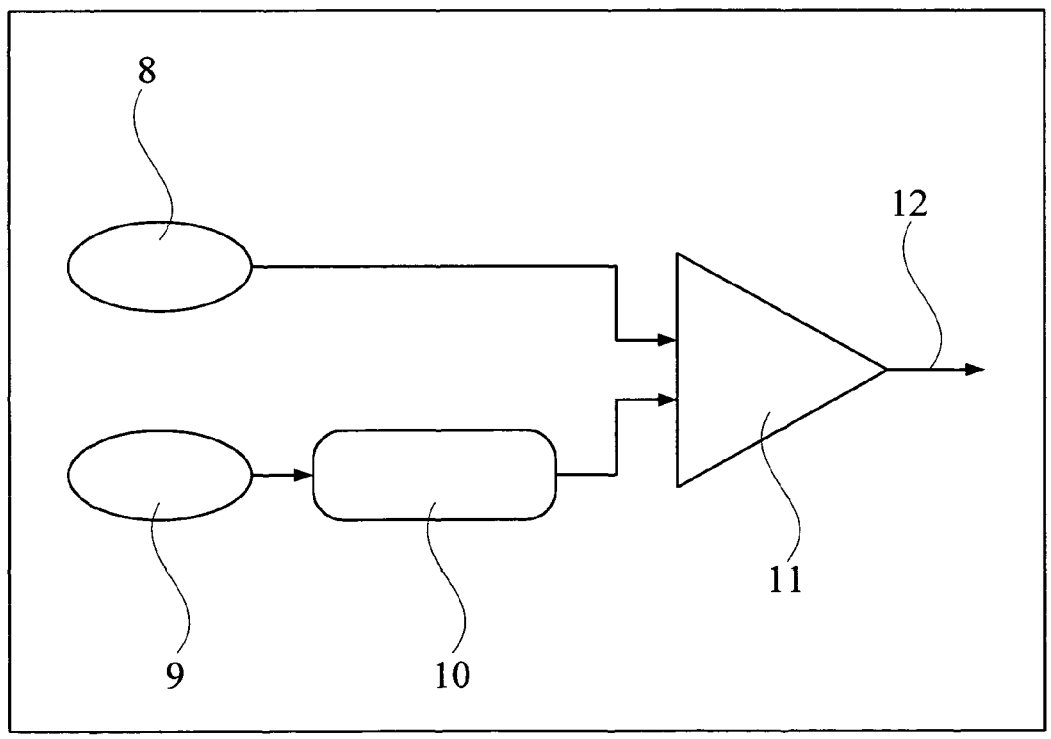
FIG. 2 is a schematic representation of the method of the drift calibration for potentiometric sensors.

Referring to FIG. 2, it shows the drift calibration method of sensor according to the present invention. The first sensor 8 and the second sensor 9 output the first sensing signal 34 and the second sensing signal 32 respectively. The signal shifting circuit 10 transforms the second sensing signal 34 to a third sensing signal 33 when the signal shifting circuit 10 receives the second signal. A fourth sensing signal is obtained from the difference between the first sensing signal 34 and the third sensing signal 33, it means that the fourth signal is the sensing signal removing drift effect.

Figure 3:
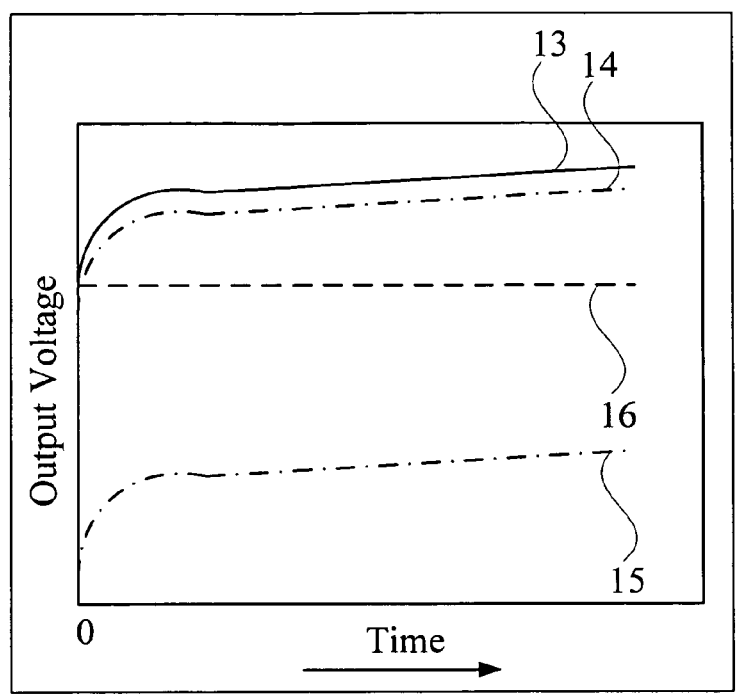
FIG. 3 is a schematic representation of the principle of the calibration for potentiometric sensors.

FIG. 3 shows the output potential and time relation plot of the sensor. The first sensing signal 13 and the second sensing signal 14 of the first sensor 8 and the second sensor 9 may change by time and drift. Therefore, the signals of the long-term measurement of the sensors can be represented as follows: "the response signal plus the drift signal". The first sensing signal 13 includes the response signal of the first sensing signal 13 and the drift signal of the first sensing signal 13; and the second sensing signal 14 includes the response signal of the signal sensing signal 14 and the drift signal of the second sensing signal 14.

The third signal 15 can be obtained by shifting the response signal of the second sensing signal 14 to zero. Thus, the third signal 15 is equal to the drift signal of the second sensing signal. The fourth signal 16 can be obtained from the difference of the first sensing signal 13 and the third sensing signal by the employment of differential circuit. The fourth signal can be represented as follows: "the response signal of the first sensing signal 13 plus the drifting signal of the first sensing signal 13 and minus the drift signal of the second sensing signal." When the drift signal of the first sensing signal 13 is equal to the drift signal of the second sensing signal 14, the fourth signal 16 is equal to the response signal of the first sensing signal 13. Therefore, the fourth signal 16 is the response signal without drift signal of sensor.

Figure 4:
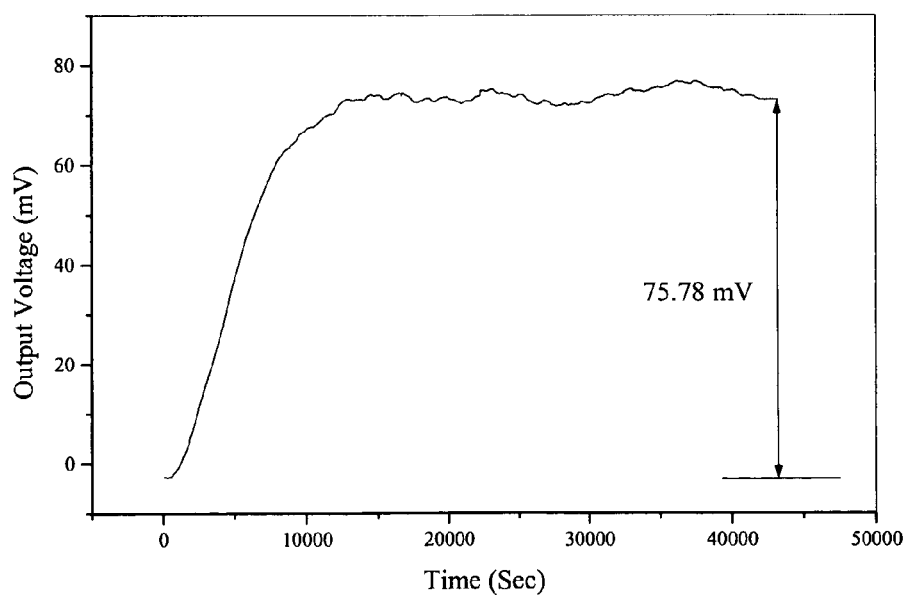
FIG. 4 is a schematic representation of the long-term output voltage of the tin oxide pH sensor in pH7 buffer solution.

According to one embodiment of the patent, the pH sensor at pH7 buffer solution for measuring 12 hours, the relation of the output potential and the measuring time as shown in FIG. 4. The pH sensor is potentiometric tin oxide pH sensor, and the instrumentation differential amplifier 6 could be the commercial IC LT1167. After 12 hours, the drift of the output potential of the potentiometric tin oxide pH sensor is 75.78 mV, which is 6.31 mV/hour.

Figure 5:
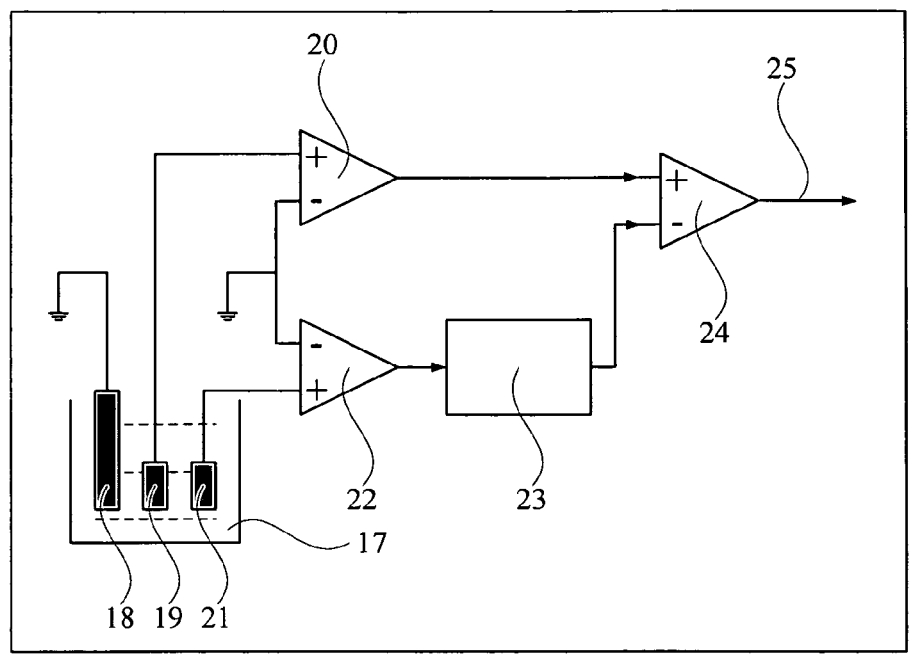
FIG. 5 is a schematic representation of the circuit of the drift calibration for potentiometric sensors.

FIG. 5 shows the circuit of the circuit of drift calibration for potentiometric sensors according to another embodiment of the patent. The circuit of drift calibration for potentiometric sensors includes a reference electrode 18, the first potentiometric sensing element 19, the second potentiometric sensing element 21, the first instrumental differential amplifier 20, the second instrumental differential amplifier 22, a voltage shifting circuit 23 and the third instrumental differential amplifier 25. Wherein the first potentiometric sensing element 19 is located in a testing solution 17, and connected to the positive input end of the first potentiometric sensing element 20. The second potentiometric sensing element 21 locates in a testing solution 17, and connects to the positive input end of the second potentiometric sensing element 22. The negative input end of the first instrumental differential amplifier 20 connects to ground, and the output end of the first instrumental differential amplifier 20 connects to the positive end of the third instrumental differential amplifier 25. The negative input end of the second instrumental differential amplifier 21 connects to ground, and the output end of the first instrumental differential amplifier 20 connects to the voltage shifting circuit 23. The other end of the voltage shifting circuit 23 connects to the negative input end of the third instrumental differential amplifier 25. The reference electrode 18 locates in a testing solution 17 with the other end connecting to ground.

The first instrumental differential amplifier 20 and the second instrumental differential amplifier 22 are readout circuits of the first potentiometric sensing element 19 and the second potentiometric sensing element 21. And the third instrumental differential amplifier 25 is applied for differential technology. The reference electrode 18 generally includes an Ag/AgCl reference electrode which is used to provide a constant reference voltage.

Figure 6:
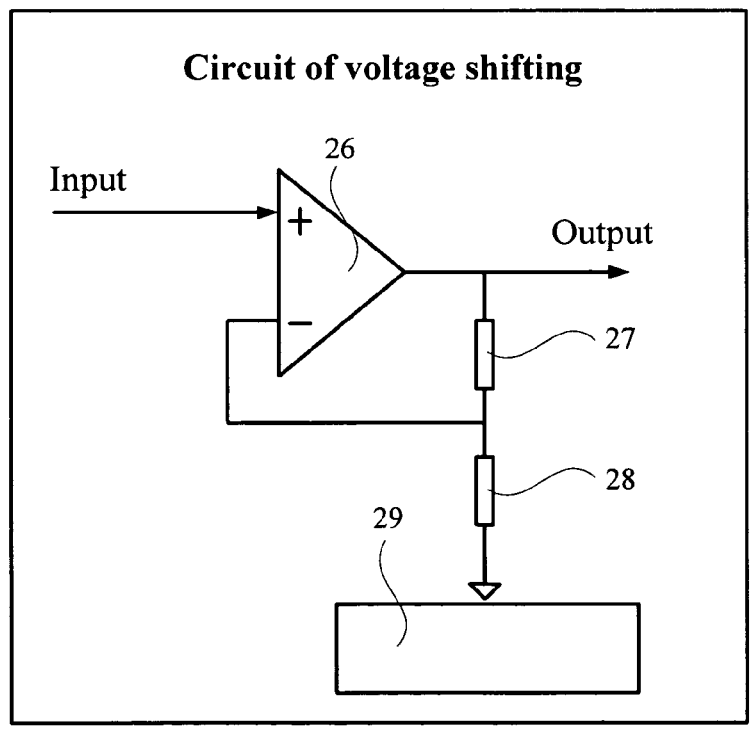
FIG. 6 is a schematic representation of the voltage shifting circuit.

The voltage shifting circuit 23 is shown in FIG. 6. The voltage is shifting by a controlled bias circuit 29 incorporated with an operation amplifier 26, which is operated with negative feedback mode. In one case, the operation amplifier is operated in negative feedback mode with the resistances 27, 28.

Figure 7:
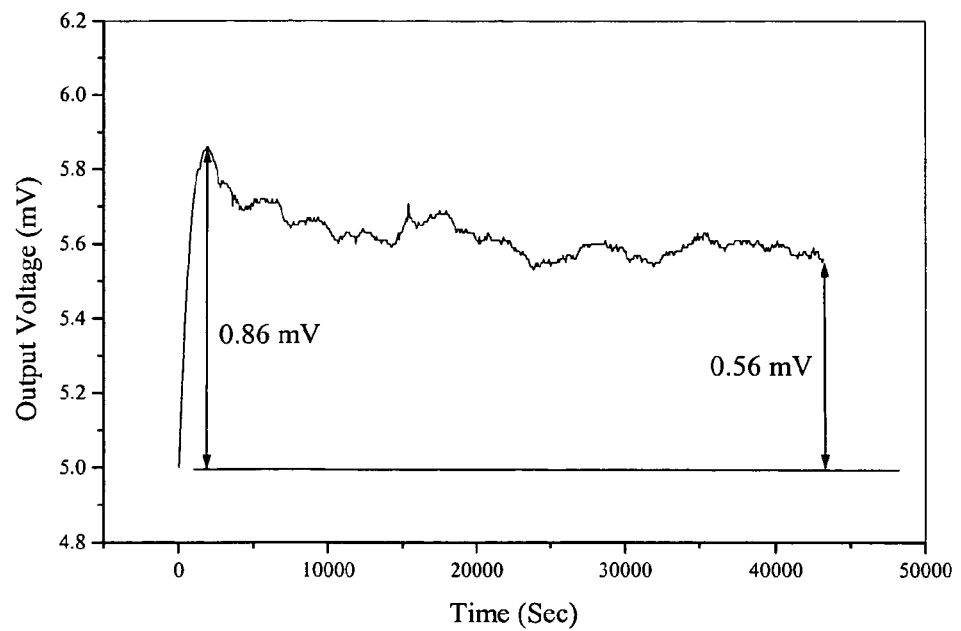
FIG. 7 is a schematic representation of the long-term output voltage of the tin oxide pH sensor after the drift calibration in pH7 buffer solution.

FIG. 7 shows the output voltage and time relation diagram of the circuit of the drift calibration according to the patent, wherein the tin oxide pH sensor locates in pH7 buffer solution for 12 hours measurement. In the period of 12 hours, the voltage drift of the tin oxide pH sensor was 0.86 mV and the drift was 0.07 mV/h.

Figure 8:
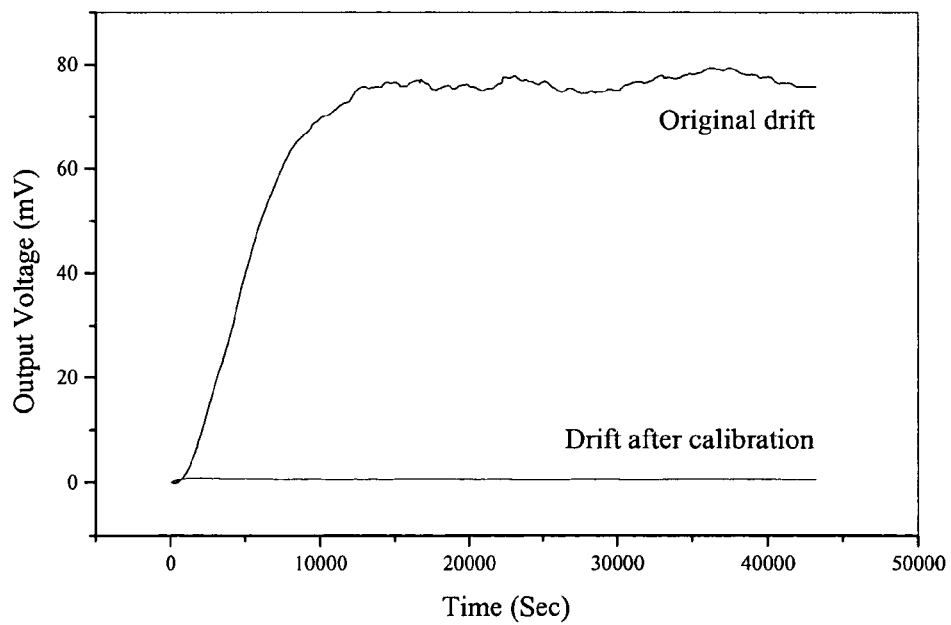
FIG. 8 is a schematic representation of the comparison between the original signal and the signal after the drift calibration of the tin oxide pH sensor.

FIG. 8 is a diagram shows the comparison between the output voltages from the tin oxide pH sensor locates in pH7 buffer solution under 12 hours measurement and the output voltage after drift calibration. The drift after the drift calibration remained 1.13% of the original drift of the tin oxide pH sensor. Therefore the drift calibration can be accomplished effectively.

Figure 9:
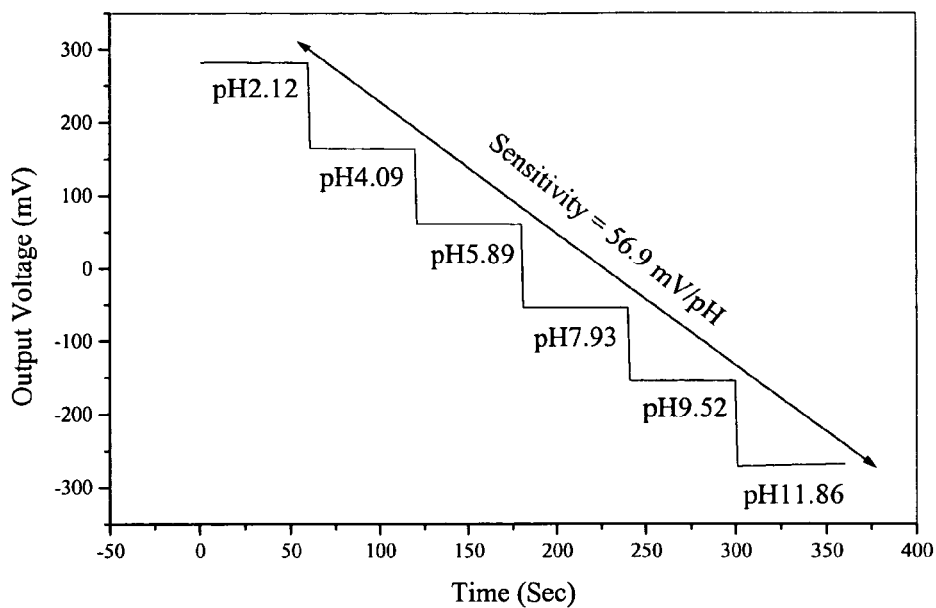
FIG. 9 is a schematic representation of the pH response voltage of the tin oxide pH sensor, which is after the drift calibration, between pH2 and pH12.

According to one embodiment, the diagram shows the response voltage of the tin oxide pH sensor, which was combined with the circuit of the drift calibration, in the range between pH2 and pH12, as shown in FIG. 9. According to the experimental results, the sensitivity of the tin oxide pH sensor was 56.9 mV/pH, and the stability of the system is 0.001 pH/h ((0.07 mV/h)/(56.9 mV/pH)=0.001 pH/h) the sensitivity incorporates with the drift obtained in FIG. 7, that is the change of output signal is 0.01 pH in the period of 10 h. Simultaneously, the circuit of the drift calibration is capable of the sensor measurement.

Figure 10:
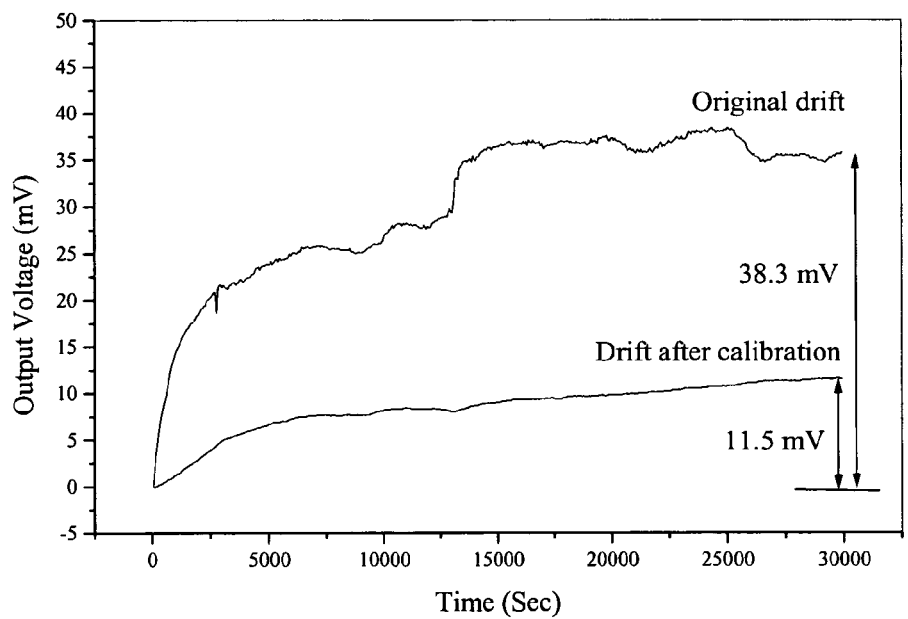
FIG. 10 is a schematic representation of the comparison between the original signal and the signal, which is after the drift calibration, of the ion-selective electrode (ISE).

Referring to FIG. 10, the diagram shows the response of the NH4+ ISE, which was combined with and without the circuit of the drift calibration in FIG. 5, the NH4+ ISE was measured at the Tris-HCl buffer solution of the ammonium concentration of 10-3 M under 8 hr. measurement. The drift of the NH4+ ISE without the circuit of the drift calibration was 38.3 mV during the period of 8 hours. Furthermore, the drift of the NH4+ ISE with the circuit of the drift calibration was 11.5 mV during the period of 8 hours. In comparison with the original drift and the drift after the drift calibration, the calibrated drift after the drift calibration remained 30.02% of the original drift. The circuit of the drift calibration is able to utilize not only on the drift calibration of the tin oxide pH sensor but also on the drift calibration of the NH4+ ISE. It indicates that the circuit of the drift calibration is suitable for the potentiometric sensors.

In conclusion, the present invention provides a calibration apparatus, which not only cancel the drift effect of the sensing signal of the potentiometric sensors in long-term measurement, but also can be the pH sensor. The calibration apparatus can be applied with potentiometric pH sensor and potentiometric ammonium ISE sensor.

Although specific embodiments have been illustrated and described, it will be obvious to those skilled in the art that various modifications may be made without departing from what is intended to be limited solely by the appended claims.

What is claimed is:

1. An apparatus for sensor calibration, comprising:
a first sensing element located in a monitoring solution for outputting a first sensing signal;
a second sensing element located in said monitoring solution for outputting a second sensor signal;
a first instrumental differential amplifier for outputting said first sensing signal, wherein a first input end of said first instrumental differential amplifier connects to said first sensing element, and a second input end connects to ground;
a second instrumental differential amplifier for outputting said second sensing signal, wherein a third input end of said second instrumental differential amplifier connects to said second sensing element, and a fourth input end connects to said ground;
a voltage shifting circuit coupled to the output end of said second instrumental differential amplifier for shifting said second operation sensing signal and outputting a third signal proportional to a sensor drift;
a third instrumental differential amplifier, wherein a fifth input end of said third instrumental differential amplifier connects to the output end of said first sensing element, and a sixth input end connects to said voltage shifting circuit for obtaining the potential difference between said first sensing signal and said third signal; and
a reference element located in said monitoring solution, wherein one end of said reference element connects to said ground for providing a constant reference voltage.

2. The apparatus in claim 1, wherein said first sensing element comprises a potentiometric sensor including a potentiometric $SnO_2$ pH sensor.

3. The apparatus in claim 1, wherein said second sensing element comprises a potentiometric sensor including a potentiometric $SnO_2$ pH sensor.

4. The apparatus in claim 1, wherein said first instrumental differential amplifier includes the instrumentation amplifier or the differential amplifier.

5. The apparatus in claim 1, wherein said second instrumental differential amplifier includes the instrumentation amplifier or the differential amplifier.

6. The apparatus in claim 1, wherein said voltage shifting circuit comprises a feedback circuit.

7. The apparatus in claim 1, wherein said third instrumental differential amplifier includes the instrumentation amplifier and the differential amplifier.

8. The apparatus in claim 1, wherein said reference element includes a Ag/AgCl reference electrode.

9. The apparatus in claim 1, wherein said first input end is a positive input end.

10. The apparatus in claim 1, wherein said second input end is a negative input end.

11. The apparatus in claim 1, wherein said third input end is a positive input end.

12. The apparatus in claim 1, wherein said fourth input end is a negative input end.

13. The apparatus in claim 1, wherein said fifth input end is a positive input end.

14. The apparatus in claim 1, wherein said sixth input end is a negative input end.

15. The apparatus in claim 1, further comprising a differential circuit wherein a fourth sensing signal is obtained from the difference between the first sensing signal and the third sensing signal and the fourth sensing signal is a response signal in which a drift effect is removed.

* * * * *